United States Patent
Uchida et al.

(10) Patent No.: US 11,543,418 B2
(45) Date of Patent: Jan. 3, 2023

(54) BIOMARKER FOR COGNITIVE DYSFUNCTION DISEASE AND METHOD FOR DETECTING COGNITIVE DYSFUNCTION DISEASE USING BIOMARKER

(71) Applicants: MCBI INC., Ibaraki (JP); Kazuhiko Uchida, Ibaraki (JP)

(72) Inventors: Kazuhiko Uchida, Ibaraki (JP); Kohji Meno, Ibaraki (JP); Hideaki Suzuki, Ibaraki (JP)

(73) Assignees: Kazuhiko Uchida, Ibaraki (JP); MCBI INC., Ibaraki (JP)

( * ) Notice: Subject to any disclaimer, the term of this patent is extended or adjusted under 35 U.S.C. 154(b) by 0 days.

(21) Appl. No.: 16/630,045

(22) PCT Filed: Jul. 13, 2017

(86) PCT No.: PCT/JP2017/025607
§ 371 (c)(1),
(2) Date: Mar. 9, 2020

(87) PCT Pub. No.: WO2019/012667
PCT Pub. Date: Jan. 17, 2019

(65) Prior Publication Data
US 2020/0200767 A1    Jun. 25, 2020

(51) Int. Cl.
G01N 33/68 (2006.01)
C07K 16/18 (2006.01)

(52) U.S. Cl.
CPC ......... G01N 33/6896 (2013.01); C07K 16/18 (2013.01); *G01N 2800/28* (2013.01)

(58) Field of Classification Search
CPC . G01N 33/6896; G01N 2800/28; C07K 16/18
See application file for complete search history.

(56) References Cited

U.S. PATENT DOCUMENTS

| | | | |
|---|---|---|---|
| 2002/0164668 A1 | 11/2002 | Durham et al. | |
| 2012/0149034 A1 | 6/2012 | Uchida et al. | |
| 2012/0283114 A1 | 11/2012 | Cohen et al. | |
| 2013/0337479 A1 | 12/2013 | Uchida et al. | |
| 2014/0273275 A1 | 9/2014 | Jacobs et al. | |

FOREIGN PATENT DOCUMENTS

| | | |
|---|---|---|
| JP | 2004-505609 A | 2/2004 |
| JP | 2004-333274 A | 11/2004 |
| JP | 2006-308533 A | 11/2006 |
| JP | 2010-271078 | 12/2010 |
| JP | 2012-132808 A | 7/2012 |
| WO | 01/69261 A2 | 9/2001 |
| WO | 2008/063369 A2 | 5/2008 |

OTHER PUBLICATIONS

Maharu Nakano et al., "The better understanding of Alzheimer's disease ", p. 33 line 21-p. 34 line 24, Nagai Shoten Co., Ltd., 2004.
N. Benkirane et al., "Antigenicity and Immunogenicity of Modified Synthetic Peptides Containing D-Amino Acid Residues", The Journal of Biological Chemistry, p. 26279-26285, vol. 268, No. 35, 0Dec. 15, 1993.
Kohji Meno et al., "Development of a Novel Blood-Based Diagnostic System for Mild Cognitive Impairment and Alzheimer's Disease Using Circulationg Biomarker Peptides", Alzheimer's Association International Conference Abstract, Jul. 16-20 Annual Conference, London, England; Jul. 14-15 Preconferences, Jul. 16-19 Exhibit Dates.
International Search Report of PCT/JP2017/025607 dated Sep. 12, 2017.
Kazuhiko Uchida et al., "Blood-based biomarker or early detection of cognitive impairment", Journal of Medical Technology, p. 1530-1536, vol. 60, No. 13, Dec. 15, 2016.
Kazuhiko Uchida et al., "Blood Biomarkers for mild cognitive impairment and Alzheimer's disease", Dementia Japan, p. 277-288, vol. 27, No. 3, Sep. 15, 2013.
Kazuhiko Uchida et al., "Japan Society for Dementia Research", Dementia Japan, p. 438, vol. 26, No. 4, Oct. 25, 2012.
The extended European Search Report mailed by European Patent Office dated Feb. 2, 2021 in corresponding European patent application No. 17917789.4 1118/ 3654038.

*Primary Examiner* — Olga N Chernyshev
(74) *Attorney, Agent, or Firm* — IP Business Solutions, LLC

(57) ABSTRACT

This invention provides a method for detecting cognitive disfunction diseases including mild cognitive impairment and Alzheimer's disease using a protein and a peptide of the protein different in the presence level in subjects having a normal cognitive function and patients suffering from cognitive disfunction diseases and a biomarker for detecting cognitive disfunction diseases including mild cognitive impairment and Alzheimer's disease containing the protein and the peptide. This invention is a biomarker for diagnosing cognitive disfunction diseases containing a prothrombin precursor protein of SEQ ID NO: 1 or a peptide THRB containing the amino acid sequence represented by SEQ ID NO: 2 which is a peptide of the protein, a diagnosis method for cognitive disfunction diseases using the biomarker, an antigen peptide represented by SEQ ID NO: 3 for creating a THRB peptide specific antibody to be used in the diagnosis method, and a cognitive disfunction disease diagnosis kit containing the THRB peptide specific antibody.

2 Claims, 4 Drawing Sheets
Specification includes a Sequence Listing.

Marker A = THRB

Marker A = THRB

Marker A = THRB

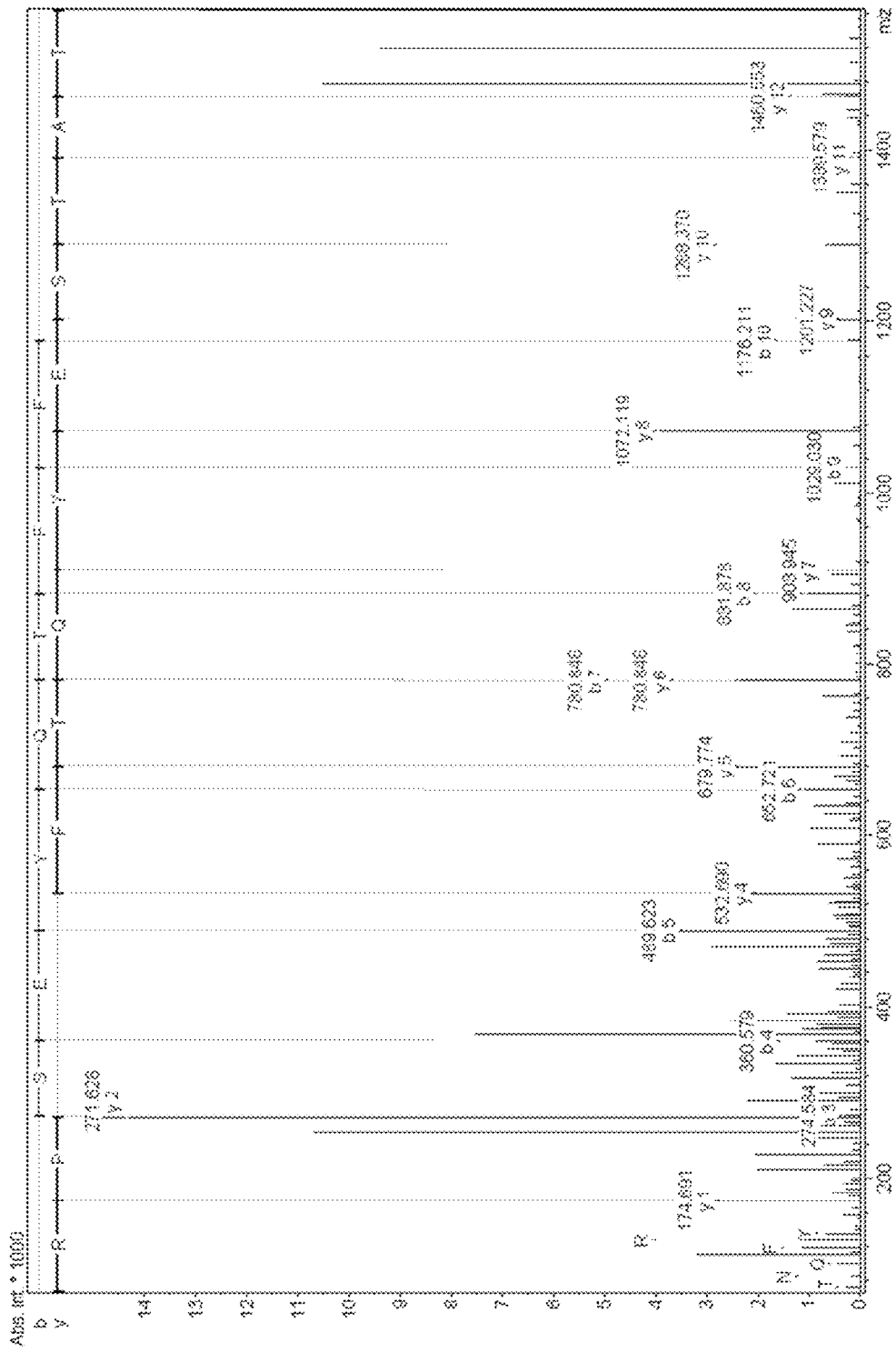
Fig. 4  Marker A = THRB

```
SEQUENCE LISTING

<160> NUMBER OF SEQ ID NOS: 29

<210> SEQ ID NO 1
<211> LENGTH: 579
<212> TYPE: PRT
<213> ORGANISM: Homo sapiens

<400> SEQUENCE: 1

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270
```

Ala Thr Ser Glu Tyr Gln Thr Phe Phe Asn Pro Arg Thr Phe Gly Ser
    275                 280                 285

Gly Glu Ala Asp Cys Gly Leu Arg Pro Leu Phe Glu Lys Lys Ser Leu
    290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
    370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
    450                 455                 460

Lys Glu Thr Trp Thr Ala Asn Val Gly Lys Gly Gln Pro Ser Val Leu
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
    530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 2
<211> LENGTH: 13
<212> TYPE: PRT
<213> ORGANISM: Homo sapiens

<400> SEQUENCE: 2

Thr Ala Thr Ser Glu Tyr Gln Thr Phe Phe Asn Pro Arg
1               5                   10

<210> SEQ ID NO 3
<211> LENGTH: 9
<212> TYPE: PRT
<213> ORGANISM: Homo sapiens

<400> SEQUENCE: 3

Thr Ala Thr Ser Glu Tyr Gln Thr Cys
1               5

<210> SEQ ID NO 4
<211> LENGTH: 14
<212> TYPE: PRT
<213> ORGANISM: Homo sapiens

<400> SEQUENCE: 4

Arg Ser Gly Gly Asn Ala Thr Leu Gln Val Asp Ser Trp Pro
1               5                   10

<210> SEQ ID NO 5
<211> LENGTH: 12
<212> TYPE: PRT
<213> ORGANISM: Homo sapiens

<400> SEQUENCE: 5

Gly Leu Asp Glu Asp Ser Asp Arg Ala Ile Glu Gly
1               5                   10

<210> SEQ ID NO 6
<211> LENGTH: 13
<212> TYPE: PRT
<213> ORGANISM: Homo sapiens

<400> SEQUENCE: 6

Gly Leu Asp Glu Asp Ser Asp Arg Ala Ile Glu Gly Arg
1               5                   10

<210> SEQ ID NO 7
<211> LENGTH: 14
<212> TYPE: PRT
<213> ORGANISM: Homo sapiens

<400> SEQUENCE: 7

Leu Ala Gly Leu Ile Phe Gly Leu Leu Thr Val Val Leu Arg
1               5                   10

<210> SEQ ID NO 8
<211> LENGTH: 19
<212> TYPE: PRT
<213> ORGANISM: Homo sapiens

<400> SEQUENCE: 8

Ala Ile Leu Ile Leu Asp Asn Asp Gly Asp Arg Leu Phe Ala Lys Tyr
1               5                   10                  15

Tyr Asp Asp

<210> SEQ ID NO 9
<211> LENGTH: 18
<212> TYPE: PRT
<213> ORGANISM: Homo sapiens

<400> SEQUENCE: 9

Pro His Ser Phe Tyr Phe Pro Gly Gln Phe Ala Phe Ser Lys Ala Leu
1               5                   10                  15

Pro Arg

<210> SEQ ID NO 10
<211> LENGTH: 19
<212> TYPE: PRT
<213> ORGANISM: Homo sapiens

```
<400> SEQUENCE: 10

Pro His Ser Phe Tyr Phe Pro Gly Gln Phe Ala Phe Ser Lys Ala Leu
1               5                   10                  15

Pro Arg Ser

<210> SEQ ID NO 11
<211> LENGTH: 12
<212> TYPE: PRT
<213> ORGANISM: Homo sapiens

<400> SEQUENCE: 11

Pro Val Arg Ala Ala Thr Ala Ser Arg Gly Ala Ser
1               5                   10

<210> SEQ ID NO 12
<211> LENGTH: 17
<212> TYPE: PRT
<213> ORGANISM: Homo sapiens

<400> SEQUENCE: 12

Ser Asp Val Pro Ser Gly Val Thr Glu Val Val Val Lys Leu Phe Asp
1               5                   10                  15

Ser

<210> SEQ ID NO 13
<211> LENGTH: 20
<212> TYPE: PRT
<213> ORGANISM: Homo sapiens

<400> SEQUENCE: 13

Arg Phe Phe Thr Arg Glu Pro Gln Asp Thr Tyr His Tyr Leu Pro Phe
1               5                   10                  15

Ser Leu Pro His
            20

<210> SEQ ID NO 14
<211> LENGTH: 25
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Oxidation of Methionine

<400> SEQUENCE: 14

Gly Val Val Pro Gly Gly Gly Leu Lys Ala Thr Met Lys Asp Asp Leu
1               5                   10                  15

Ala Asp Tyr Gly Gly Tyr Asp Gly Gly
            20                  25

<210> SEQ ID NO 15
<211> LENGTH: 23
<212> TYPE: PRT
<213> ORGANISM: Homo sapiens

<400> SEQUENCE: 15

Ser Ser Pro Ile Leu Asp Leu Ser Glu Ser Gly Leu Cys Arg Leu Glu
1               5                   10                  15

Glu Val Phe Arg Ile Pro Ser
            20

<210> SEQ ID NO 16
```

```
<211> LENGTH: 14
<212> TYPE: PRT
<213> ORGANISM: Homo sapiens

<400> SEQUENCE: 16

Ala Pro Val Ile His Gln Glu Met Ile Gly Gly Leu Arg Asn
1               5                   10

<210> SEQ ID NO 17
<211> LENGTH: 16
<212> TYPE: PRT
<213> ORGANISM: Homo sapiens

<400> SEQUENCE: 17

Pro Gly Arg Gln Ser Gln Glu Gly Ala Gly Leu Pro Ser His His Gly
1               5                   10                  15

<210> SEQ ID NO 18
<211> LENGTH: 17
<212> TYPE: PRT
<213> ORGANISM: Homo sapiens

<400> SEQUENCE: 18

Glu Met Phe Gly Gly Leu Asp Ile Cys Ala Val Lys Ala Val His Ser
1               5                   10                  15

Lys

<210> SEQ ID NO 19
<211> LENGTH: 11
<212> TYPE: PRT
<213> ORGANISM: Homo sapiens

<400> SEQUENCE: 19

Ala Ala Pro Pro Gly Ala Glu Gly Asn Arg Thr
1               5                   10

<210> SEQ ID NO 20
<211> LENGTH: 14
<212> TYPE: PRT
<213> ORGANISM: Homo sapiens

<400> SEQUENCE: 20

Arg Val Ser Leu Phe Ser Leu Ala Phe Gly Asp Asp Ala Asp
1               5                   10

<210> SEQ ID NO 21
<211> LENGTH: 17
<212> TYPE: PRT
<213> ORGANISM: Homo sapiens

<400> SEQUENCE: 21

Lys Leu Ala Glu Leu Pro Ala Ala Ala Gln Pro Ser Ala Glu Asp Ser
1               5                   10                  15

Asp

<210> SEQ ID NO 22
<211> LENGTH: 21
<212> TYPE: PRT
<213> ORGANISM: Homo sapiens

<400> SEQUENCE: 22

Thr Ala Thr Ser Glu Tyr Gln Thr Phe Phe Asn Pro Arg Thr Phe Gly
1               5                   10                  15
```

Ser Gly Glu Ala Asp
            20

<210> SEQ ID NO 23
<211> LENGTH: 20
<212> TYPE: PRT
<213> ORGANISM: Homo sapiens

<400> SEQUENCE: 23

Ala Val Arg Gly Ser Pro Ala Ile Asn Val Ala Val His Val Phe Arg
1               5                   10                  15

Lys Ala Ala Asp
            20

<210> SEQ ID NO 24
<211> LENGTH: 16
<212> TYPE: PRT
<213> ORGANISM: Homo sapiens

<400> SEQUENCE: 24

Gln Thr Ala Ser Gly Gln Ala Leu Lys Gly Asp Gly Gly Leu Tyr Ser
1               5                   10                  15

<210> SEQ ID NO 25
<211> LENGTH: 16
<212> TYPE: PRT
<213> ORGANISM: Homo sapiens

<400> SEQUENCE: 25

Asn Gly Phe Lys Ser His Ala Leu Gln Leu Asn Asn Arg Gln Ile Arg
1               5                   10                  15

<210> SEQ ID NO 26
<211> LENGTH: 16
<212> TYPE: PRT
<213> ORGANISM: Homo sapiens

<400> SEQUENCE: 26

Asn Gly Phe Lys Ser His Ala Leu Gln Leu Asn Asn Arg Gln Ile Arg
1               5                   10                  15

<210> SEQ ID NO 27
<211> LENGTH: 23
<212> TYPE: PRT
<213> ORGANISM: Homo sapiens

<400> SEQUENCE: 27

Ser Ser Ser Tyr Ser Lys Gln Phe Thr Ser Ser Thr Ser Tyr Asn Arg
1               5                   10                  15

Gly Asp Ser Thr Phe Glu Ser
            20

<210> SEQ ID NO 28
<211> LENGTH: 25
<212> TYPE: PRT
<213> ORGANISM: Homo sapiens

<400> SEQUENCE: 28

Ser Ser Ser Tyr Ser Lys Gln Phe Thr Ser Ser Thr Ser Tyr Asn Arg
1               5                   10                  15

Gly Asp Ser Thr Phe Glu Ser Lys Ser
            20                  25

```
<210> SEQ ID NO 29
<211> LENGTH: 26
<212> TYPE: PRT
<213> ORGANISM: Homo sapiens

<400> SEQUENCE: 29

Ser Ser Ser Tyr Ser Lys Gln Phe Thr Ser Ser Thr Ser Tyr Asn Arg
1               5                   10                  15

Gly Asp Ser Thr Phe Glu Ser Lys Ser Tyr
            20                  25
```

BIOMARKER FOR COGNITIVE DYSFUNCTION DISEASE AND METHOD FOR DETECTING COGNITIVE DYSFUNCTION DISEASE USING BIOMARKER

TECHNICAL FIELD

The present invention relates to biomarkers which are peptides usable for detecting cognitive dysfunction diseases including mild cognitive impairment and Alzheimer's disease and a method for detecting the cognitive dysfunction diseases using the biomarkers.

BACKGROUND ART

A major prior art as a means for using samples exhibiting in vivo conditions which are normal and are not normal for determining a difference between them is a technology generally used in extracorporeal diagnostic agents. Most of the extracorporeal diagnostic agents are used in diagnostic examination in which blood components are analyzed as biomarkers. The prior art in this field involves measuring the presence level of a single certain protein or a so-called peptide having a molecular weight of 10,000 or less in the blood or, in the case of enzymatic proteins, measuring the activity to thereby obtain a marked difference between a normal sample (healthy individual) and a disease sample, which serves as an aid in the diagnosis. More specifically, the level or the activity/the levels or the activities of a single or multiple certain proteins or peptides is/are measured in samples derived from a certain number of healthy and diseased individuals beforehand to determine the abnormal and normal ranges. Then, a sample to be evaluated is measured by the same method, and then inspection and evaluation are performed based on the range, abnormal or normal, in which the measured value is included.

Specific measurement methods include an enzyme linked immunosorbent assay (ELISA) and a chemiluminescent immunoassay (CLIA) in which the level/levels of a single or multiple certain proteins or peptides in a sample which has been or has not been diluted beforehand is/are measured based on the colorimetric level of the sample using a specific primary antibody or secondary antibody labeled with an enzyme which develops a color when reacting with a substrate, a radioimmunoassay (RIA) measuring the certain protein or peptide levels using a radioisotope bound to the primary antibody or the secondary antibody, an enzyme activity assay, when the protein is an enzyme, in which a substrate is directly added and the resultant products are measured based, for example, on color development, and the like. These methods using antibodies are referred to as "enzyme-, fluorescence-, or radioactive-labeled antibody methods". There is also a method of analyzing an enzymatic degradation product from a substrate using a high performance liquid chromatography (HPLC). Moreover, there is also an LC-MS/MS method in which the HPLC is combined with a mass spectrometer and a selected reaction monitoring (SRM)/multiple reaction monitoring (MRM) method using the same. Moreover, there is also a method in which a sample is appropriately pretreated and then subjected to a two-dimensional polyacrylamide gel electrophoresis (2D-PAGE) to separate proteins or peptides, and thereafter the intended protein or peptide is subjected to silver staining, coomassie blue staining, or immunostaining using a corresponding antibody (western blotting) to thereby measure the concentration in the sample. Moreover, there is a technique of fractionating a biological sample by column chromatography and analyzing the proteins and the peptides contained in the fraction by mass spectrometry. Moreover, instead of the column chromatography, there is also a method of performing a pretreatment using a protein chip for mass spectrometry and a method of performing a pretreatment using magnetic beads for mass spectrometry.

The present inventors also have developed an immuno-MS method in which beads (including magnetic beads) are bound to an antibody against the target protein or peptide to thereby capture the target protein or peptide, and thereafter the target protein or peptide is allowed to elute from the beads and measured by the mass spectrometry. For the purpose of analyzing an intact protein, a method has been reported in which the above-described method is used to perform mass spectrometry after degradation, for example, with trypsin or the like (see Patent Document 1). However, in all the above-described methods, a direct fractionation is performed utilizing the nature of an intact protein or a specifically adsorbing protein molecule is selected and analyzed by mass spectrometry.

Cognitive dysfunction diseases typified by Alzheimer's disease are rapidly prevailing also in Japan in response to an increase in the population of the aged. The population was about 1,300,000 in 1995, and then increased to about 1,900,000 in 2005, and is assumed to reach about 3,000,000 in 2020. The Alzheimer's disease is believed to account for 60 to 90% of the cognitive dysfunction diseases. This disease is becoming a social problem because it makes a patient suffer not only from loss of memory but also from destruction of personality to thereby impair the social life function of the patient. In Japan, donepezil hydrochloride, which is an anti-acetylcholinesterase inhibitor, was approved in the end of 1999, and it became possible to retard the decrease in the cognitive function at a high probability by an early administration. In Alzheimer's disease, an early diagnosis is a greatest challenge for achieving the effectiveness of current therapeutic methods or drugs which will be developed in future.

The major diagnostic criteria for Alzheimer's disease (DSM IV) made by American Psychiatric Association are described below.

A. The development of multiple cognitive deficits manifested by both:
(1) memory impairment (impaired ability to learn new information or to recall previously learned information)
(2) one or more of the following cognitive impairments:
   a) aphasia (language disorder)
   b) apraxia (impaired ability to carry out motor activities despite intact motor function)
   c) agnosia (failure to recognize or identify objects despite intact sensory function)
   d) disturbance in executive functioning (i.e., planning, organizing, sequencing, abstracting)
B. The cognitive deficits in Criteria A(1) and A(2) each cause significant impairment in social or occupational functioning and represent a significant decline from a previous level of functioning (Non-Patent Document 1).

There are various diseases associated with Alzheimer's disease (AD). Since a cognitive disease, such as AD, exhibits a slowly developing reduction in the cognitive functions, there is a condition which should be referred to as a precursory condition of the cognitive disease. Such a condition is referred to as mild cognitive impairment (MCI). Based on the data in United States, the MCI in hospital visitors for amnesia is advanced to the AD within 1 year in 10 to 15% of the patients, and within 4 years in about 50%.

The precursory condition of the AD is mostly included in amnesic MCI. According to the current definitions, the MCI is regarded as a condition in which complaint relating to a reduction in the cognitive functions is given but there is no particular difficulty in everyday life. Frontotemporal dementia (FTD) is characterized by reduced cognitive functions together with a selfish behavior regardless of the circumstance, which is in contrast to the AD in which a patient makes an effort to be in harmony with the circumstance. The FTD includes Pick's disease in which a pick body is histologically observed in cerebral cortex. Dementia with Lewy Bodies (DLB) is characterized by progressive memory disturbance and visual cognitive impairment, such as hallucination. Based on the diagnosis of clinical signs, 10 to 30% of cognitive disease is the DLB, which is second highest after the Alzheimer-type cognitive disease (AD) among senile degenerative cognitive disease types. Histologically, the Lewy Body is characteristically present in the cerebrum. The FTD and the DLB exhibit a cognitive disease and are of a dementia type, and therefore are referred to also as dementia-type neurological diseases (Non-Patent Document 1).

In the present invention, when collectively referred to as cognitive dysfunction diseases, it is intended that the MCI, the AD, and the dementia-type neurological diseases are also included.

Tests widely used in diagnosing the cognitive disease are Revised Hasegawa's Dementia Scale (HDS-R) and MMSE (Mini-Mental State Examination) in which questions are given to a subject and the diagnosis is made based on the results. HDS was revised in 1991, and then became to be referred to as HDS-R. This is constituted from questions in 9 terms, which are intended to test orientation, encoding, calculation ability, memory/recall, and common sense. 23 points or less on a maximum scale of 30 points are considered to be reflecting a suspected cognitive disease. On the other hand, MMSE was established in United States for diagnosing dementia and involves orientation, memorizing ability, calculation ability, speech ability, understanding of diagrams, and the like. It gives 11 questions and 23 points or less on a maximum scale of 30 points, similarly to the HDS-R, are considered to be reflecting a suspected cognitive disease. The results of both the tests are believed to be in a relatively good agreement with each other. These question-based diagnostic methods are used merely for screening, and do not give any definitive diagnoses, and any of the HDS-R or the MMSE is not used in classification of severity (Non-Patent Document 1).

Image-based diagnostic methods include CT/MRI observing morphological abnormality in brain, such as encephalatrophy and enlarged vadum and ventricle, cerebral blood flow scintigraphy (single photon emission computed tomography, SPECT) observing the cerebral blood flow level, and positron emission tomography (PET) observing oxygen consumption/glucose consumption. The SPECT and the PET are nuclear medicine-based methods and believed to be able to detecting abnormality before onset of morphological abnormality (Non-Patent Document 1). Nevertheless, these image-based diagnostic methods have drawbacks due to difficulty in being performed in every medical facility because of special devices required therefor. In addition, they are not sufficient for giving an objective decision because the decision differs from physician to physician observing the image.

As described above, the diagnosis of the cognitive diseases, such as the AD, currently depends on a method which is less objective and requires expensive instruments and is not successful in screening for identifying the disease. When a biomarker enabling an objective diagnosis using a readily obtainable patient's sample, such as blood (including serum and plasma), is found herein, a screening can be performed to thereby enable an early detection of cognitive dysfunction diseases which is the most challenging in these days. It is an object of the present invention to provide such a novel biomarker and a method for detecting cognitive disfunction diseases using the biomarker.

CITATION LIST

Patent Document

[Patent Document 1] JP-A No. 2004-333274
[Patent Document 2] JP-A No. 2006-308533

Non-Patent Document

[Non-Patent Document 1] "YOKUWAKARU ALZHEIMER'S DISEASE", edited by K. Nakano, H. Mizusawa, Nagai Shoten, 2004
[Non-Patent Document 2] N. Benkirane et al., J. Biol. Chem. Vol. 268, 26279-26285, 1993.

SUMMARY OF THE INVENTION

Technical Problem

It is an object of the present invention to provide a method for detecting cognitive dysfunction diseases including mild cognitive impairment and Alzheimer's disease using peptides which are present or absent or are present in different levels in non-demented controls (subjects including healthy humans who may have any disease but not have mental diseases including cognitive dysfunction diseases and matched with the demented controls in the age and the sex, hereinafter abbreviated as NDC) and patients having cognitive dysfunction diseases and to provide a biomarker for detecting cognitive disfunction diseases including mild cognitive impairment and Alzheimer's disease containing the peptides.

Solution to Problem

The present inventors have performed an extensive examination about a method for detecting cognitive dysfunction diseases and have found peptides capable of detecting cognitive dysfunction diseases including mild cognitive impairment and Alzheimer's disease in serum. The peptides found in the present invention have significance as biomarkers when detected not only in serum but also in other biological samples, such as blood, plasma, cerebrospinal fluid, and urine. Simultaneously, source proteins from which the above-describes peptides are derived (hereinafter also referred to as "intact proteins") also have a significance as biomarkers.

Specifically, the present inventors have found that a peptide containing the amino acid sequence represented by SEQ ID NO: 2 (TATSEYQTFFNPR) is usable as a biomarker for the diagnosis of cognitive dysfunction diseases.

The present inventors have further succeeded in measuring a large number of proteins, peptides, or peptide fragments at once by subjecting the proteins, the peptides or the peptide fragments to a two-dimensional liquid chromatography (2D-LC)-MALDI-TOF-MS (mass spectrometry)

method or an immuno-MS method, and thus have accomplished the present invention.

More specifically, aspects of the present invention are as follows.

[1] biomarker for detecting a cognitive dysfunction disease, which is a peptide containing the amino acid sequence represented by SEQ ID NO: 2 or a peptide containing the amino acid sequence represented by SEQ ID NO: 2 in which 1 to 3 amino acids are deleted, substituted, and/or added.

[2] The biomarker for detecting a cognitive dysfunction disease according to [1], in which the cognitive dysfunction disease is mild cognitive impairment or Alzheimer's disease.

[3] A peptide containing the amino acid sequence represented by SEQ ID NO: 3.

[4] A monoclonal antibody, which is obtained by immunizing a mouse with a peptide containing the amino acid sequence represented by SEQ ID NO: 3.

[5] A method for detecting a cognitive dysfunction disease including detecting a peptide containing the amino acid sequence represented by SEQ ID NO: 2 or a peptide containing the amino acid sequence represented by SEQ ID NO: 2 in which 1 to 3 amino acids are deleted, substituted, and/or added in a living body sample extracted from a subject.

[6] The method for detecting a cognitive dysfunction disease according to [5], in which the detection is performed using a monoclonal antibody obtained by immunizing a mouse with a peptide containing the amino acid sequence represented by SEQ ID NO: 3.

[7] The method for detecting a cognitive dysfunction disease according to [5] or [6] including comparing a detection result of a biomarker for detecting a cognitive dysfunction disease which is the peptide containing the amino acid sequence represented by SEQ ID NO: 2 or the peptide containing the amino acid sequence represented by SEQ ID NO: 2 in which 1 to 3 amino acids are deleted, substituted, and/or added in the living body sample extracted from the subject and a detection result of the biomarker in a living body sample of a normal person not suffering from the cognitive dysfunction disease.

[8] The method for detecting a cognitive dysfunction disease according to any one of [5] to [7], in which the detection is performed by an immunoblotting method, a western blotting method, an enzyme-, fluorescence-, or radioactive-labeling method, a mass spectrometry method, an immuno-MS method, or a surface plasmon resonance method.

[9] A kit for detecting a cognitive dysfunction disease containing an antibody or an aptamer specifically bound to a peptide containing the amino acid sequence represented by SEQ ID NO: 2 or a peptide containing the amino acid sequence represented by SEQ ID NO: 2 in which 1 to 3 amino acids are deleted, substituted, and/or added.

[10] The kit for detecting a cognitive dysfunction disease according to [9], in which the antibody is a monoclonal antibody obtained by immunizing a mouse with a peptide containing the amino acid sequence represented by SEQ ID NO: 3.

Advantageous Effects of Invention

According to the present invention, by measuring the presence or the level of a biomarker containing a peptide containing the amino acid sequence represented by SEQ ID NO: 2 or a peptide containing the amino acid sequence represented by SEQ ID NO: 2 in which 1 to 3 amino acids are deleted, substituted, and/or added in a living body sample derived from a subject, it can be diagnosed when the biomarker is present or increases as compared with the inside of a living body sample of a subject not suffering from a mental disease that the subject is suffering from a cognitive dysfunction disease including mild cognitive impairment or Alzheimer's disease.

Moreover, the present invention provides a diagnostic system in which both the accuracy and the specificity are extremely high. The present invention enables high-accuracy diagnosis for a cognitive dysfunction disease for which a specific inspection method about a living body sample, such as blood, has not been found. Furthermore, the biomarker of the present invention is highly useful also in judging the efficacy of a drug.

BRIEF DESCRIPTION OF DRAWINGS

FIG. 4 is an MS/MS spectrum by a TOF/TOF mass spectrometer.

DESCRIPTION OF EMBODIMENTS

Figure 1:
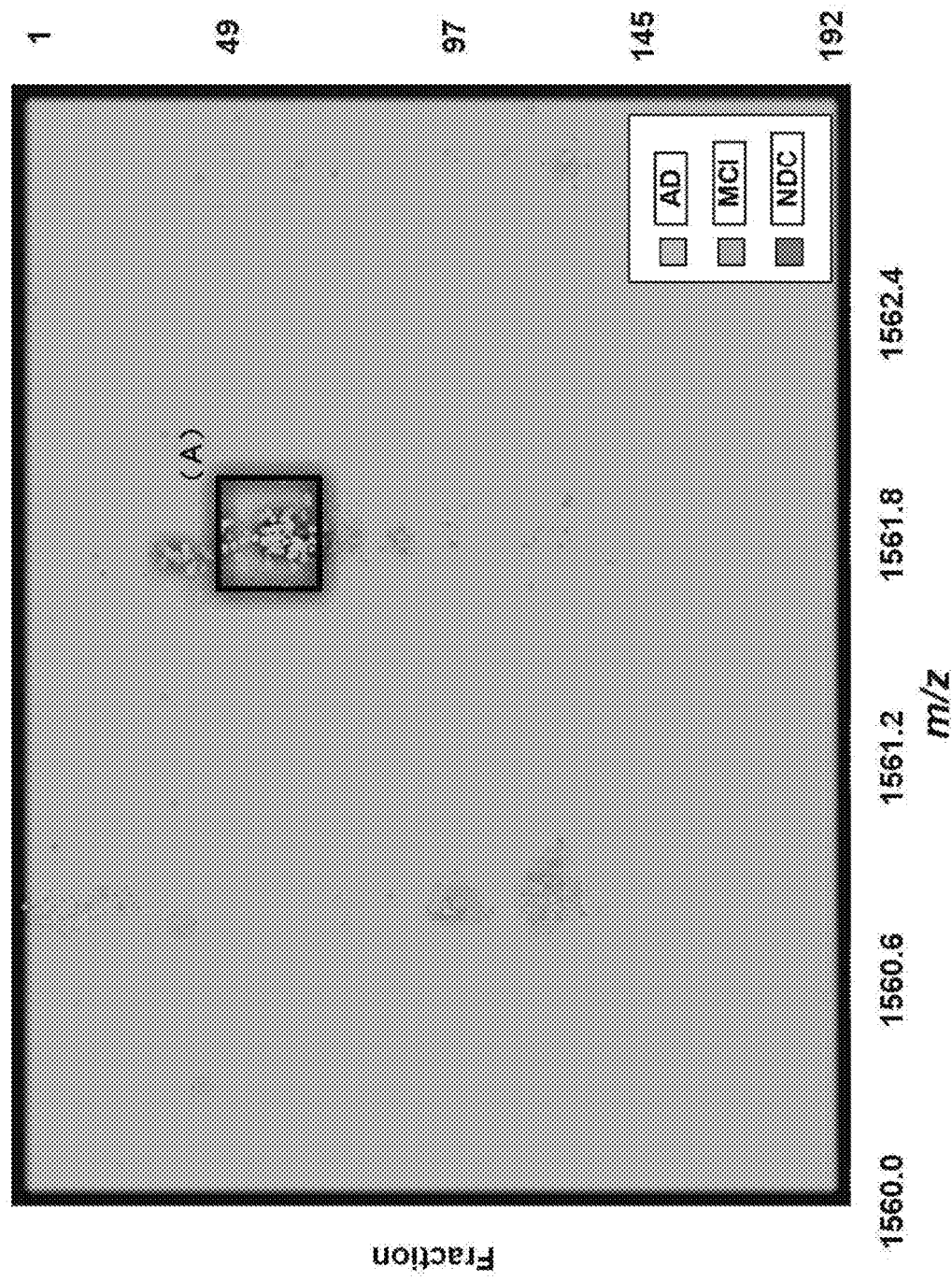
FIG. 1 is a figure illustrating the retention time of a mass peak and m/z in a C18 reverse phase chromatography (second dimension) of Marker A detected in serum of a subject.

The present invention is a method for diagnosing whether a subject is suffering from a cognitive dysfunction disease by detecting a peptide containing the amino acid sequence represented by SEQ ID NO: 2 or a peptide containing the amino acid represented by SEQ ID NO: 2 in which 1 to 3 amino acids are deleted, substituted, and/or added or the level thereof and simultaneously measuring a change in the level thereof in a living body sample of the subject, when the subject is suffering from a cognitive dysfunction disease.

Herein, the peptide generally refers to one having amino acids having a molecular weight of 10,000 or less bound to each other or one having several to about 50 amino acid residues or less. In the present invention, a partial peptide of an intact protein peptide derived from a peptide is usable as a biomarker for detecting cognitive dysfunction diseases. When referred to as the partial peptide, the partial peptide is a peptide having a partial amino acid sequence which is a part of the amino acid sequence possessed by the intact protein and having a molecular weight of 10,000 or less. In the present invention, the partial peptide of an intact protein refers to a peptide having a partial amino acid sequence which is a part of the amino acid sequence possessed by the intact protein and is sometimes formed as a partial peptide in a process of expression and synthesis through transcription and translation or sometimes formed as a digestion product peptide due to an in vivo digestion after being synthesized as an intact protein. This may be due to deregulation of the mechanism for synthesis and control of the protein in the presence of in vivo condition which is not normal, as in a cognitive dysfunction disease or the like. More specifically, the present invention is also a method for discriminating whether a subject is in a normal condition or is suffering from a cognitive dysfunction disease using an in vivo protein expression and synthesis, and/or digestion as an index and also, in the case of suffering from the cognitive dysfunction disease, evaluating the degree to which the disease has been advanced. In the present invention, the "detection of cognitive dysfunction diseases" means evaluation and discrimination of whether a subject is suffering from a cognitive dysfunction disease, i.e., performing diagnosis. Moreover, the evaluation of the risk at which the subject will suffer from a more serious cognitive dysfunction and the like may be included.

In the method of the present invention, the intact protein usable as a biomarker for detecting cognitive dysfunction diseases, Prothrombin (SEQ ID NO: 1) is specifically mentioned and a peptide fragment having 5 or more amino acid residues which is the partial peptide of the intact protein may be used for the same purpose.

Moreover, the peptide usable as the biomarker for detecting cognitive dysfunction diseases is the peptide containing the amino acid sequence represented by SEQ ID NO: 2 or the peptide containing the amino acid sequence represented by SEQ ID NO: 2 in which 1 to 3 amino acids are deleted, substituted, and/or added.

Herein, in the present invention, although the intact proteins and the peptides described above are used as a marker, proteins or peptides containing an amino acid sequence in which one or several amino acids is/are deleted, substituted, or added in each amino acid sequence thereof are also included and the proteins or the peptides are also usable as the biomarker in the method of the present invention.

As used herein, "one or several" means "one to three", "one or two", or "one".

Furthermore, these peptides usable as the biomarker for detecting cognitive dysfunction diseases include peptide fragments generated from the amino acid sequence represented by SEQ ID NO: 1 or SEQ ID NO: 2 having 5 or more amino acid residues. The reason why "5 or more amino acid residues" is designated in the "peptide fragment having 5 or more amino acid residues" is based on the following description in Non-Patent Document 2. This Non-Patent Document 2 reports that a peptide resulting from substituting K for R in the histone H3's C-terminal (130 to 135) amino acid residue sequence IRGERA and a peptide CGG-GERA resulting from deletion of IR and ligation of CGG to GERA were recognized by an antibody obtained by using a peptide IRGERA as an immunogen. This reflects that the recognition of the antigenicity is accomplished by a peptide containing 4 or more amino acid residues. While, in the present invention, the number of the residues is 5 or more which is larger by one to give more generality to those other than the histone H3's C-terminal, it is important to cover even such a low molecular weight peptide when the detection and separation are performed by an immunological procedure, such as an immunoblotting method, an ELISA method, and an immuno-MS method.

To an intact protein or a peptide, a sugar chain is sometimes added. Such a protein or a peptide to which a sugar chain was added is also usable as the biomarker for detecting cognitive dysfunction diseases.

In the present invention, the biomarker may be quantified or a qualification may be performed to determine the presence or absence.

As a method for separating the biomarker in a biological sample, such as serum, in the present invention, a two-dimensional electrophoresis or a two-dimensional chromatography is usable. The two kinds of chromatography in this case may be selected from known chromatography, such as ion exchange chromatography, reverse phase chromatography, and gel filtration chromatography. Moreover, the biomarker can also be quantified by an SRM/MRM method using an LC-MS/MS method. In addition, by the use of the immuno-MS method including binding beads (including magnetic beads) developed by the present inventors to antibodies against target proteins or peptides to thereby capture the proteins or peptides to be measured, allowing the proteins or peptides to elute from the beads, and then measuring the proteins or peptides by mass spectrometry, the presence or absence or the level of the target proteins, protein fragments, or peptides can be conveniently evaluated without using two-dimensional electrophoresis or chromatography.

The method of the present invention also enables the evaluation of a cognitive dysfunction of a subject at a mild stage and is useful also in preventive medicine. When a mental therapy or a medication given to a patient suffering from a cognitive dysfunction disease serves to suppress the progression of the impairment, the suppression is reflected on the levels of the proteins/peptides in biological samples, such as serum. By measuring the levels, the effectiveness of the treatment can be evaluated and judged.

The type and the level of proteins in a biological sample can be measured by various methods. When the target protein (including a protein fragment and a peptide) is specified and an antibody thereagainst (primary antibody) is obtained, the following methods are usable.

As the antibody, a polyclonal antibody or a monoclonal antibody is can be produced by immunizing an antibody production animal (for example, rabbit or mouse) with a protein containing the amino acid sequence represented by SEQ ID NO: 1, a peptide containing the amino acid sequence represented by SEQ ID NO: 2, or a peptide containing partial peptides thereof (for example, peptide containing the amino acid sequence represented by SEQ ID NO: 3), followed by purification.

1. Immunoblotting Method

This is the simplest method. Serially diluted serum samples are prepared, and then an aliquot (about 1 microliter) is dropped onto an appropriate membrane, such as a nitrocellulose membrane, followed by drying in air. After treatment with a blocking solution containing a protein, such as BSA, or a peptide followed by washing, reaction with a primary antibody, and then washing, a labeled secondary antibody for detecting the primary antibody is reacted. After washing the membrane, the label is visualized and the concentration is measured.

2. Western Blotting Method

After performing one-dimensional or two-dimensional gel electrophoresis including an isoelectric focusing or SDS-PAGE, the separated protein or peptide is once transferred onto an appropriate membrane, such as a PVDF membrane, and a primary antibody and a labeled secondary antibody are used to perform a procedure analogous to the above-described immunoblotting method to thereby measure the presence level of the target protein.

3. ELISA Method

An antibody against a protein or its partial peptide is bound to a support, such as a microtiter plate, which has been chemically modified in a specific manner, a sample is subjected to a serial dilution, and then an appropriate amount thereof is added to the microtiter plate to which the antibody is bound, followed by incubation. Thereafter, the protein and the peptide which were not captured are washed out. Then, a secondary antibody having a fluorescent or chemiluminescent substance or an enzyme bound thereto is added and incubated. For detection, each substrate is added, and thereafter the fluorescent or chemiluminescent substance or the enzymatic reaction-induced visible light is measured to thereby accomplish evaluation and judgement. Instead of the antibody, a substance capable of binding to the protein or peptide may be used. For example, an aptamer or the like is usable.

Further methods (see Patent Document 2) are also exemplified below, but the present invention is not limited thereto.

4. Method Using Microarray (Microchip)

A microarray is a generic name of devices in which substances capable of binding to a substance to be measured are aligned (arrayed) and immobilized on a support (substrate). In the case of the present invention, an antibody against a protein and a peptide or an aptamer may be aligned and immobilized. In the measurement, a biological sample is added to an immobilized antibody and the like, and a protein or a peptide to be measured is bound onto the microarray, and then a secondary antibody having a fluorescent or chemiluminescent substance or an enzyme bound thereto is added and incubated. For detection, each substrate is added and thereafter the fluorescent or chemiluminescent substance or the enzymatic reaction-induced visible light may be measured.

5. Mass Spectrometry Method

In a mass spectrometry method, for example, an antibody against a certain protein and peptide is bound to a microbead or a substrate (protein chip) which has been chemically modified in a specific manner. The microbead may be a magnetic bead. Materials of the substrate are not limited. The antibody to be used may be all of (1) an antibody recognizing only the full-length of a certain protein, (2) an antibody recognizing only a certain peptide, and (3) an antibody recognizing both the certain protein and the certain peptide, or a combination of the above-described (1) and (2), (1) and (3), or (2) and (3). An appropriate amount of a sample is added as it is or after serial dilution with a buffer solution to a microbead or a substrate to which the antibody has been bound, and then incubated. Thereafter, the non-captured protein and peptide are washed out. Thereafter, the protein and the peptide captured on the microbead or the substrate are analyzed by mass spectrometry using MALDI-TOF-MS, SELDI-TOF-MS, and the like to thereby measure the peak mass numbers and the peak intensities of the protein, protein fragment, and the peptide. By adding a specific amount of an appropriate internal standard substance to the starting biological sample, measuring its peak intensity, and then calculating the ratio to the peak intensity of the target substance, the concentration in the starting biological sample can be known. This method is referred to as an immuno-MS method. A sample is separated by HPLC as it is or after diluting it with a buffer solution or partially removing the protein, and then quantification can be performed by mass spectrometry using an electrospray ionization (ESI) method. In such a case, by means of an absolute quantification by the SRM/MRM method using an isotopically labeled internal standard peptide, the concentration in the sample can be known.

Furthermore, in addition to the above-described methods, a protein and a peptide can be analyzed also by a method using a two-dimensional electrophoresis, a method using surface plasmon resonance, and the like.

The present invention also includes a method for detecting cognitive dysfunction diseases using the presence or absence or the level of the above-described biomarker as an index by subjecting a biological sample taken from a subject to a two-dimensional electrophoresis or a surface plasmon resonance.

In the above-described methods, the peptide containing the amino acid sequence represented by SEQ ID NO: 2 according to the present invention may be combined as appropriate with one or two or more of other biomarkers for detecting cognitive dysfunction diseases. Examples of the other biomarkers for detecting cognitive dysfunction diseases include those described in International Publication No. WO2010/134308 and International Publication No. WO2012/086197, for example.

Biomarkers particularly preferable for the combination among the biomarkers described in these publications are as follows:

```
Neurexin-2-beta precursor-derived peptide NRX2B
Amino acid sequence:
                                          (SEQ ID NO: 4)
RSGGNATLQVDSWP Prothrombin precursor-derived peptide THRB (R-)
Amino acid sequence:
                                          (SEQ ID NO: 5)
GLDEDSDRAIEG Prothrombin precursor-derived peptide THRB (R+)
Amino acid sequence:
                                          (SEQ ID NO: 6)
GLDEDSDRAIEGR Pendrin-derived peptide S26A4
Amino acid sequence:
                                          (SEQ ID NO: 7)
LAGLIFGLLTVVLR Coatomer subunit zeta-1-derived peptide COPZ1
Amino acid sequence:
                                          (SEQ ID NO: 8)
AILILDNDGDRLFAKYYDD Retinoic acid receptor responder protein 2
precursor-derived peptide RARR2 (S-)
Amino acid sequence:
                                          (SEQ ID NO: 9)
PHSFYFPGQFAFSKALPR Retinoic acid receptor responder protein 2
precursor-derived peptide RARR2 (S+)
Amino acid sequence:
                                         (SEQ ID NO: 10)
PHSFYFPGQFAFSKALPRS Gelsolin precursor-derived peptide GELS
Amino acid sequence:
                                         (SEQ ID NO: 11)
PVRAATASRGAS Clusterin precursor-derived peptide CLUS (N-term
SDVP)
Amino acid sequence:
                                         (SEQ ID NO: 12)
SDVPSGVTEVVVKLFDS Clusterin precursor-derived peptide CLUS (N-term
RFFT)
Amino acid sequence:
                                         (SEQ ID NO: 13)
RFFTREPQDTYHYLPFSLPH Eukaryotic translation initiation factor 3 subunit
J-derived peptide EIF3J
Amino acid sequence:
                                         (SEQ ID NO: 14)
GVVPGGGLKATMKDDLADYGGYDGG + Oxidation (M)

Leucine-rich repeat-containing protein 27-derived
peptide LRC27
Amino acid sequence:
                                         (SEQ ID NO: 15)
SSPILDLSESGLCRLEEVFRIPS
```

```
Complement C3-derived peptide CO3
Amino acid sequence:
                                         (SEQ ID NO: 16)
APVIHQEMIGGLRN Transcription factor AP-2 gamma-derived peptide
AP2C
¶ Amino acid sequence:
                                         (SEQ ID NO: 17)
PGRQSQEGAGLPSHHG Synapsin-3-derived peptide SYN3
Amino acid sequence:
                                         (SEQ ID NO: 18)
EMFGGLDICAVKAVHSK Oxytocin receptor-derived peptide OXYR
Amino acid sequence:
                                         (SEQ ID NO: 19)
AAPPGAEGNRT Inter-alpha-trypsin inhibitor heavy chain H5-like
protein-derived peptide ITH5L
Amino acid sequence:
                                         (SEQ ID NO: 20)
RVSLFSLAFGDDAD E3 ubiquitin-protein ligase HERC2-derived peptide
HERC2
Amino acid sequence:
                                         (SEQ ID NO: 21)
KLAELPAAAQPSAEDSD Prothrombin-derived peptide THRB
Amino acid sequence:
                                         (SEQ ID NO: 22)
TATSEYQTFFNPRTFGSGEAD Transthyretin-derived peptide TTHY
Amino acid sequence:
                                         (SEQ ID NO: 23)
AVRGSPAINVAVHVFRKAAD Tumor necrosis factor receptor superfamily member
16-derived peptide TNR16
Amino acid sequence:
                                         (SEQ ID NO: 24)
QTASGQALKGDGGLYS Complement C4-derived peptide CO4-1
Amino acid sequence:
                                         (SEQ ID NO: 25)
NGFKSHALQLNNRQIR Complement C4-derived peptide CO4-2
Amino acid sequence:
                                         (SEQ ID NO: 26)
APLQPVTPLQLFEGRRN Fibrinogen alpha chain-derived peptide FIBA-1
Amino acid sequence:
                                         (SEQ ID NO: 27)
SSSYSKQFTSSTSYNRGDSTFES Fibrinogen alpha chain-derived peptide FIBA-2
Amino acid sequence:
                                         (SEQ ID NO: 28)
SSSYSKQFTSSTSYNRGDSTFESKS Fibrinogen alpha chain-derived peptide FIBA-3
Amino acid sequence:
                                         (SEQ ID NO: 29)
SSSYSKQFTSSTSYNRGDSTFESKSY.
```

The present invention also provides a kit for detecting cognitive dysfunction diseases containing an antibody or an aptamer specifically bound to the peptide containing the amino acid sequence represented by SEQ ID NO: 2 or the peptide containing the amino acid sequence represented by SEQ ID NO: 2 in which 1 to 3 amino acids are deleted, substituted, and/or added.

The technology according to the present invention also includes a device capable of detecting the biomarker in the above-described biological samples (for example, detecting device, measuring device, analyzing device, and the like). The device according to the present technology is desirably provided with an antibody- or aptamer-immobilizing portion (capturing portion) and a measuring portion. The antibody- or aptamer-immobilizing portion preferably has a solid support, such as a glass slide and a 96-well titer plate, to which the antibody or the aptamer is immobilized. The measuring portion is preferably provided with a light detecting means corresponding to the detection target, such as a spectrophotometer and fluorescence spectrophotometer.

The device of the present technology may include an analyzing portion analyzing the obtained data. The analyzing portion preferably includes a data processing device and analysis software.

Furthermore, a controlling portion including a CPU and the like provided in the device of this disclosure or a system connectable thereto (for example, personal computer, computer network system, and the like) is provided with a program capable of implementing methods for detecting and diagnosing, for example, the cognitive dysfunction diseases of the present technology described above, a memory or a system storing such a program, or the like.

The present invention enables the judgment of a cognitive dysfunction of a subject. The present technology also enables the evaluation of a cognitive dysfunction of a subject at a mild stage, and thus is useful also in preventive medicine. Furthermore, when a mental therapy or a medication given to a patient suffering from a cognitive dysfunction disease serves to suppress the progression of the impairment, the suppression is reflected on the levels of the proteins/peptides in biological samples, such as serum. By measuring the levels, the effectiveness of the treatment can be evaluated and judged, and screening for a drug discovery target biomolecule becomes possible.

The present technology can also employ the following configurations.

[1]

A method for diagnosing a cognitive dysfunction disease, assisting the diagnosis, and treating the cognitive dysfunction disease includes a. extracting a living body sample from a subject, b. bringing an antibody produced by immunizing an antibody production animal (for example, mouse or rabbit) with a peptide containing the amino acid sequence represented by SEQ ID NO: 2 or a peptide containing the amino acid sequence represented by SEQ ID NO: 2 in which 1 to 3 amino acids are deleted, substituted, and/or added, an antibody produced by immunizing the antibody production animal (for example, mouse and rabbit) with a peptide containing the amino acid sequence represented by SEQ ID NO: 3, or an aptamer specifically bound to the peptide containing the amino acid sequence represented by SEQ ID NO: 2 or the peptide containing the amino acid sequence represented by SEQ ID NO: 2 in which 1 to 3 amino acids are deleted, substituted, and/or added into contact with the living body sample to detect the presence of a biomarker for detecting the cognitive dysfunction disease represented by SEQ ID NO: 2 in the living body sample, c. when the presence of the biomarker for detecting a cognitive dysfunction disease represented by SEQ ID NO: 2 is detected in the living body sample, diagnosing that the subject is suffering from the cognitive dysfunction disease or has a high possibility of being suffering from the cognitive dysfunction disease, and d. giving an anti-acetylcholinesterase inhibitor to the subject who has been diagnosed to be suffering from the cognitive dysfunction disease or has a high possibility of being suffering from the cognitive dysfunction disease.

[2]

The method for diagnosing a cognitive dysfunction disease and assisting the diagnosis according to [1], in which the cognitive dysfunction disease is mild cognitive impairment or Alzheimer's disease.

[3]

The method for diagnosing a cognitive dysfunction disease and assisting the diagnosis according to [1], in which the living body sample is blood, plasma, or serum.

[4]

A method for diagnosing a cognitive dysfunction disease, assisting the diagnosis, and treating the cognitive dysfunction disease includes a. extracting a living body sample from a subject, b. bringing an antibody produced by immunizing an antibody production animal (for example, rabbit or mouse) with a peptide containing the amino acid sequence represented by SEQ ID NO: 2 or a peptide containing the amino acid sequence represented by SEQ ID NO: 2 in which 1 to 3 amino acids are deleted, substituted, and/or added, an antibody produced by immunizing the antibody production animal (for example, mouse and rabbit) with a peptide containing the amino acid sequence represented by SEQ ID NO: 3, or an aptamer specifically bound to the peptide containing the amino acid sequence represented by SEQ ID NO: 2 or the peptide containing the amino acid sequence represented by SEQ ID NO: 2 in which 1 to 3 amino acids are deleted, substituted, and/or added into contact with the living body sample to measure a biomarker for detecting the cognitive dysfunction disease represented by SEQ ID NO: 2 in the living body sample, c. when the presence level of the biomarker for detecting the cognitive dysfunction disease containing the peptide containing the amino acid sequence represented by SEQ ID NO: 2 or the peptide containing the amino acid sequence represented by SEQ ID NO: 2 in which 1 to 3 amino acids are deleted, substituted, and/or added in the living body sample extracted from the subject is larger than the presence level of the biomarker for detecting the cognitive dysfunction disease in a living body sample extracted from a person not suffering from the cognitive dysfunction disease, diagnosing that the subject is suffering from the cognitive dysfunction disease or has high possibility of being suffering from the cognitive dysfunction disease, and d. giving an anti-acetylcholinesterase inhibitor to the subject who has been diagnosed to be suffering from the cognitive dysfunction disease or has high possibility of being suffering from the cognitive dysfunction disease.

[5]

The method for diagnosing a cognitive dysfunction disease, assisting the diagnosis, and treating the cognitive dysfunction disease according to [4], in which the cognitive dysfunction disease is mild cognitive impairment or Alzheimer's disease.

[6]

The method for diagnosing a cognitive dysfunction disease, assisting the diagnosis, and treating the cognitive dysfunction disease according to [4], in which the living body sample is blood, plasma, or serum.

[7]

A method for diagnosing a cognitive dysfunction disease and assisting the diagnosis includes a. extracting a living body sample from a subject, b. bringing an antibody produced by immunizing an antibody production animal (for example, mouse or rabbit) with a peptide containing the amino acid sequence represented by SEQ ID NO: 2 or a peptide containing the amino acid sequence represented by SEQ ID NO: 2 in which 1 to 3 amino acids are deleted, substituted, and/or added, an antibody produced by immunizing the antibody production animal (for example, mouse and rabbit) with a peptide containing the amino acid sequence represented by SEQ ID NO: 3, or an aptamer specifically bound to the peptide containing the amino acid sequence represented by SEQ ID NO: 2 or the peptide containing the amino acid sequence represented by SEQ ID NO: 2 in which 1 to 3 amino acids are deleted, substituted, and/or added into contact with the living body sample to detect the presence of a biomarker for detecting the cognitive dysfunction disease represented by SEQ ID NO: 2 in the living body sample, and c. when the presence of the biomarker for detecting a cognitive dysfunction disease represented by SEQ ID NO: 2 is detected in the living body sample, diagnosing that the subject is suffering from the cognitive dysfunction disease or has high possibility of being suffering from the cognitive dysfunction disease.

[8]

The method for diagnosing a cognitive dysfunction disease and assisting the diagnosis according to [7], in which the cognitive dysfunction disease is mild cognitive impairment or Alzheimer's disease.

[9]

The method for diagnosing a cognitive dysfunction disease and assisting the diagnosis according to [7], in which the living body sample is blood, plasma, or serum.

[10]

A method for diagnosing a cognitive dysfunction disease and assisting the diagnosis includes a. extracting a living body sample from a subject, b. bringing an antibody produced by immunizing an antibody production animal (for example, mouse or rabbit) with a peptide containing the amino acid sequence represented by SEQ ID NO: 2 or a peptide containing the amino acid sequence represented by SEQ ID NO: 2 in which 1 to 3 amino acids are deleted, substituted, and/or added, an antibody produced by immunizing the antibody production animal (for example, mouse and rabbit) with a peptide containing the amino acid sequence represented by SEQ ID NO: 3, or an aptamer specifically bound to the peptide containing the amino acid sequence represented by SEQ ID NO: 2 or the peptide containing the amino acid sequence represented by SEQ ID NO: 2 in which 1 to 3 amino acids are deleted, substituted, and/or added into contact with the living body sample to measure a biomarker for detecting the cognitive dysfunction disease represented by SEQ ID NO: 2 in the living body sample, and c. when the presence level of the biomarker for detecting the cognitive dysfunction disease containing the peptide containing the amino acid sequence represented by SEQ ID NO: 2 or the peptide containing the amino acid sequence represented by SEQ ID NO: 2 in which 1 to 3 amino acids are deleted, substituted, and/or added in the living body sample extracted from the subject is larger than the presence level of the biomarker for detecting the cognitive dysfunction disease in a living body sample extracted from a person not suffering from the cognitive dysfunction disease, diagnosing that the subject is suffering from the cognitive dysfunction disease or has high possibility of being suffering from the cognitive dysfunction.

[11]

The method for diagnosing a cognitive dysfunction disease and assisting the diagnosis according to [10], in which the cognitive dysfunction disease is mild cognitive impairment or Alzheimer's disease.

[12]

The method for diagnosing a cognitive dysfunction disease and assisting the diagnosis according to [10], in which the living body sample is blood, plasma, or serum.

EXAMPLES

Hereinafter, the present invention is described in more detail based on Examples. Examples described below illustrate examples of typical Examples of the present invention and the scope of the present invention should not be narrowly interpreted by Examples.

<Search of Cognitive Dysfunction Disease Diagnostic Marker Peptide by Two-Dimensional Liquid Chromatography-Mass Spectrometry (2D-LC-MALDI-TOF-MS)>

(1) Serum Sample

Serum samples of 20 AD (Alzheimer's disease) samples, 20 MCI (mild cognitive impairment) samples, 20 NDC (subject having a normal cognitive function matched with the AD patients in the age and the sex, non-demented control) samples, and 10 ODD (Other demented disease) samples were used. Furthermore, for the ODD, 10 serum samples of each of Dementia with Lewy Bodies and Frontotemporal dementia were used.

(2) Method

475 µl of 0.1% trifluoroacetic acid (TFA) was added to 25 µl of each serum, and then boiled at 100° C. for 15 minutes. Thereafter, in order to collect peptides having a molecular weight of 10,000 or less, ultrafiltration was performed using YM-10 of Millipore Corporation.

Next, the analysis by the 2D-LC-MALDI-TOF-MS method was performed as follows. More specifically, samples collected by the ultrafiltration were fractionated into 382 fractions per sample using a two-dimensional HPLC (SCX cation exchange column in the first dimension and C18 reverse phase column in the second dimension). In the SCX cation exchange column, the sample was fractionated into two fractions. More specifically, SCX 1 is a flow-through fraction and SCX 2 is a fraction eluted at a salt concentration of 100%.

The two fractions fractionated by the SCX each were fractionated into 191 fractions by the C18 reverse phase column chromatography. One fraction was eluted in 6 seconds. The retention time was obtained by multiplying Number of eluted fractions-1 by 6 seconds.

All the samples were spotted on a well on a MALDI target plate (MTP AnchorChip™ 600/384 plate (BRUKER DALTONICS)) for a MALDI TOF/TOF mass spectrometer (ultraflex TOF/TOF, BRUKER DALTONICS) using a spotting robot (AccuSpot, SHIMADZU) connected online while being mixed with a matrix solution (α-cyano-hydroxycinnamic acid, α-CHCA and cocrystallized.

After mounted to the ultraflex TOF/TOF, laser was emitted to automatically measure the mass and the peak area (including a normalization process described below) in the mass in a reflectron mode. The peak area was normalized by 250 fmole of bradykinin 1-7 per well added to the matrix solution beforehand and set as an Area value. More specifically, a value obtained by dividing the peak area in the specific mass of the sample by the peak area obtained from the bradykinin 1-7 was set as the Area value. The Area value corresponds to 25 µl of sample serum.

The detection of the peptides different in the presence level (differential analysis) in serum among groups was performed using a DeView™ (MCBI) which is multi-group statistical analysis software developed by us.

In the peptide in which the difference was observed in the presence level, the amino acid sequence was determined by the MS/MS using the ultraflex TOF/TOF and an intact protein or peptide which is the origin thereof was identified.

(3) Results

The results of performing the differential analysis by the DeView software about data obtained by subjecting the serum of each subject to the 2D-LC-MALDI-TOF-MS are described below.

FIG. 1 is a figure in which the horizontal axis represents the mass per unit charge (m/z) and the vertical axis represents the number of fractions (Fraction) in the reverse phase column chromatography in the second dimension about the spectrum measured by MALDI-TOF-MS for the 191 fractions obtained by fractionating the fractions fractionated first (SCX 1), among the fractions fractionated into the two fractions with the SCX cation exchange column in the first dimension, by the C18 reverse phase column in the second dimension.

The dots in the figure each are the TOF-MS peak derived from each subject. A portion where the dots gathered is specified as the peak derived from one peptide having the same m/z and the same number of fractions within an error range, which is indicated as a cluster. A group of the dots in the rectangle illustrated in FIG. 1(A) is a cluster of Marker A.

The dots in the cluster can be regarded to have the same m/z and the same retention time within an error range and is specified to be derived from the same peptide.

Figure 2:
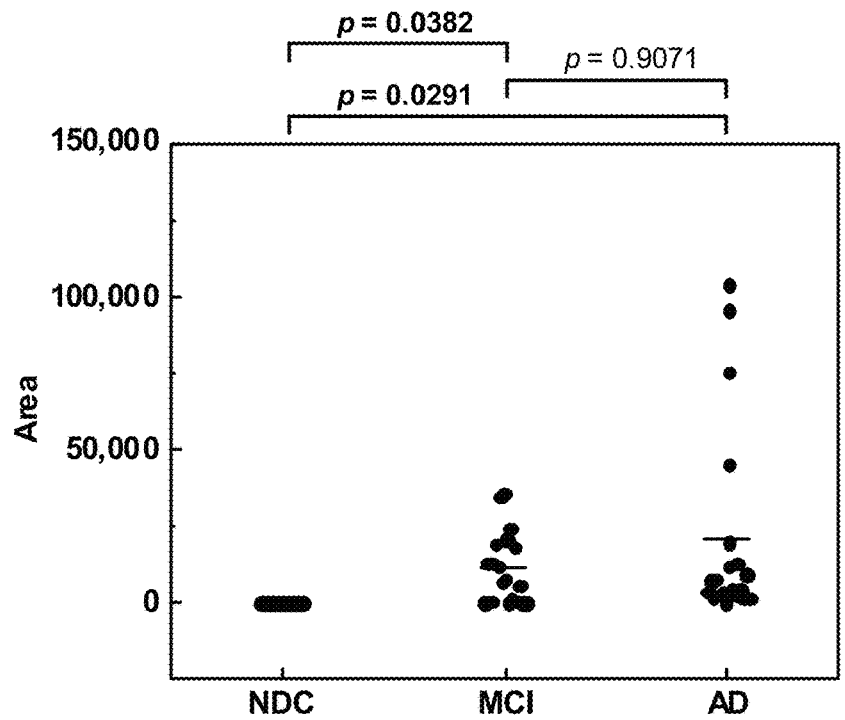
FIG. 2A is a figure illustrating the differential analysis results of Marker A between NDC, MCI and AD.
FIG. 2B is a figure illustrating the differential analysis results of Marker A between NDC, AD and ODD.
Figure 2:
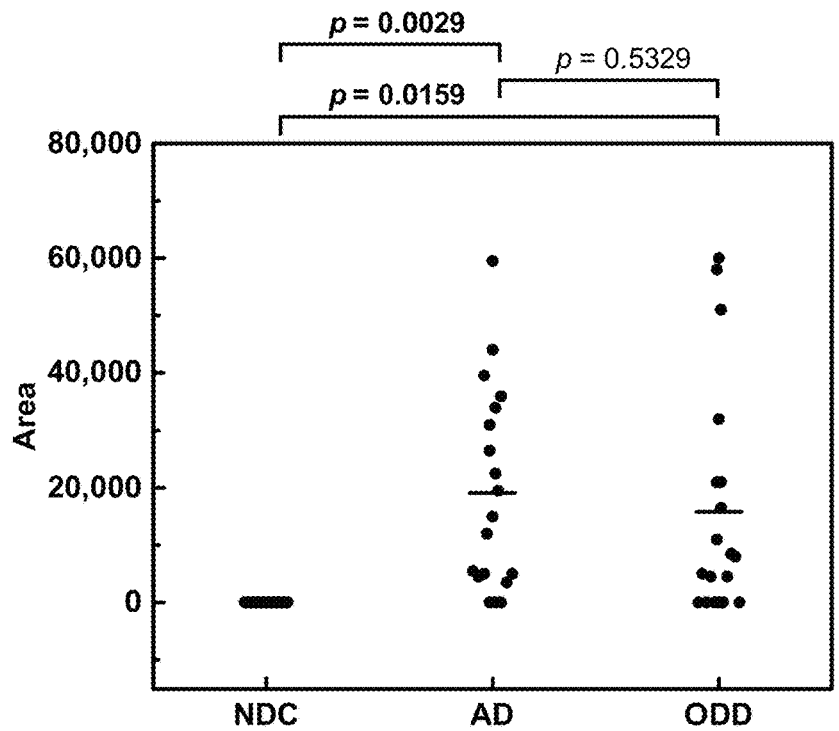

FIG. 2 illustrate the differential analysis results of the Marker A. The Marker A is a Prothrombin-derived peptide THRB as represented in the amino acid sequence obtained as a result of the MS/MS analysis of FIG. 4. FIG. 2(A) illustrates a comparison among subjects having a normal cognitive function (NDC), mild cognitive impairment (MCI), and Alzheimer type dementia patients (AD). FIG. 2(B) illustrates a comparison among the NDC, the AD, and the other dementia patients (ODD).

The Marker A is a Prothrombin-derived peptide THRB as illustrated later in FIG. 4. FIG. 2(A) illustrates a comparison among the NDC, the MCI, and the AD. FIG. 2(B) is a comparison among the NDC, the AD, and the ODD. FIGS. 2(A) and 2(B) illustrate the results of different experiments, in which the same samples were used in both the experiments for the NDC and the AD (i.e., the reproducibility of the measurement results are illustrated about the NDC and the AD).

In FIG. 2(A), the Marker A showed a statistically significant increase in the MCI and AD patients rather than the NDC ($p<0.05$ in a t-test).

In FIG. 2(B), it was found that the Marker A significantly increased in the AD and the ODD rather than the NDC.

From the results of FIG. 2, the analysis by a receiver operating characteristic curve (ROC curve) was performed in order to evaluate the useful level as a biomarker of the Marker A.

FIGS. 3(A) and 3(B) are the ROC curves in a comparison between NDC vs. AD and NDC vs. MCI, respectively.

The usefulness as a biomarker becomes higher as the area value of the lower side of the ROC curve (AUC of ROC) (hereinafter referred to as "AUC value") is closer to 1.

The typical values of the sensitivity and the specificity are values of the coordinates (open square in the figures) of the dots on the ROC curves in which, when a straight line is drawn on the ROC curves from the 100% point on the y-axis, the distance is the minimum in FIGS. 3(A) and 3(B). A cutoff value giving the point serves as a threshold value useful for the discrimination between different groups. The sensitivity and the specificity (i.e., the above-described typical values) at that time serve as an index of the usefulness of the biomarker together with the AUC value.

In FIG. 3(A), the sensitivity as the typical value was 100%, the specificity as the typical value was 100%, and the AUC value was 1.0 in NDC vs. AD. In FIG. 3(B), the sensitivity as the typical value was 90%, the specificity as the typical value was 100%, and the AUC value was 0.95 in NDC vs. MCI.

The results above showed that the marker A is useful for distinguishing the AD patients and the MCI patients from the subjects having a normal cognitive function (NDC). Moreover, it was clarified that the marker A is useful also for distinguishing the NDC and the other dementia (ODD).

In particular, the MCI is a preceding stage of the AD, and therefore it is considered that the Marker A (THRB) is very useful as a marker for diagnosing and detecting a subject who may shift to the AD at an early stage.

FIG. 4 illustrates the MS/MS analysis results analyzed by the ultraflex TOF/TOF type mass spectrometer for the Marker A. The amino acid sequence of the THRB and b-ions and y-ions appearing in the MS/MS spectrum are illustrated in the upper side of FIG. 4.

Signals indicating y-ions, b-ions, and a-ions sufficiently appeared, and thus the amino acid sequence was able to be easily judged. The search by Mascot was performed for the results, so that it was clarified that a protein or a peptide which is the origin thereof (hereinafter, referred to as intact protein or peptide) was identified to be a Prothrombin precursor and the detected peptide contains the amino acid sequence TATSEYQTFFNPR derived from the protein. About the detected peptide, THRB which is the UniProt Entry Name is used as an abbreviated name of a peptide name.

A set of two amino acid sequences of the THRB are shown below. The first sequence is the amino acid sequence of the intact protein of the THRB and the second sequence is the sequence of the detected peptide. An underline portion of the first sequence corresponds to the sequence of the detected peptide. The amino acid sequence starting with (0001) indicates the N-terminal side sequence.

[1] Prothrombin-Derived Peptide THRB

Figure 3:
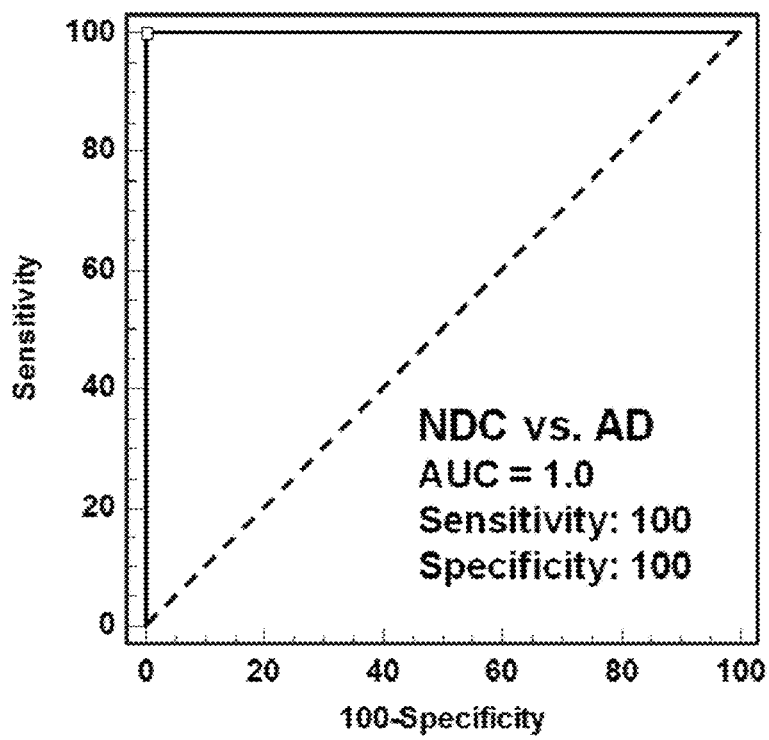
FIG. 3A is a graph illustrating ROC curves of Marker A (SEQ ID NO: 2, THRB) in NDC vs AD.
FIG. 3B is a graph illustrating ROC curves of Marker A (SEQ ID NO: 2, THRB) in NDC vs MCI.
Figure 3:
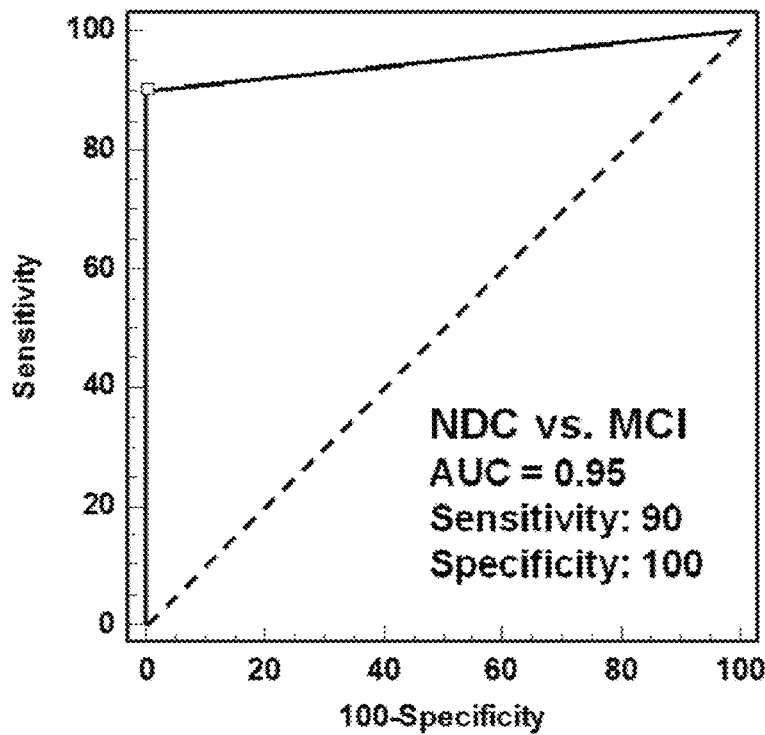

With respect to the Area value of the THRB of SEQ ID NO: 2, the cognitive dysfunction diseases (AD, MCI, DLB, FTD) show statistically significantly high values as compared with the NDC (t-test, p<0.05) (FIG. 2), and thus it was found that the THRB of SEQ ID NO: 2 is useful for discriminating the cognitive dysfunction disease (AD, MCI, DLB, FTD) patients from the subjects having normal cognitive function (NDC). According to the analysis by the receiver operating characteristic curves, it is clarified that the THRB of SEQ ID NO: 2 is useful for discriminating the AD and MCI patients from the subjects having normal cognitive function (NDC) (FIG. 3).

[Intact protein/peptide]
(SEQ ID NO: 1)

```
0001 ANTFLEEVRK GNLERECVEE TCSYEEAFEA LESSTATDVF
     WAKYTACETA
0051 RTPRDKLAAC LEGNCAEGLG TNYRGHVNIT RSGIECQLWR
     SRYPHKPEIN
0101 STTHPGADLQ ENFCRNPDSS TTGPWCYTTD PTVRRQECSI
     PVCGQDQVTV
0151 AMTPRSEGSS VNLSPPLEQC VPDRGQQYQG RLAVTTHGLP
     CLAWASAQAK
0201 ALSKHQDFNS AVQLVENFCR NPDGDEEGVW CYVAGKPGDF
     GYCDLNYCEE
0251 AVEEETGDGL DEDSDRAIEG RTATSEYQTF FNPRTFGSGE
     ADCGLRPLFE
0301 KKSLEDKTER ELLESYIDGR IVEGSDAEIG MSPWQVMLFR
     KSPQELLCGA
0351 SLISDRWVLT AAHCLLYPPW DKNFTENDLL VRIGKHSRTR
     YERNIEKISM
0401 LEKIYIHPRY NWRENLDRDI ALMKLKKPVA FSDYIHPVCL
     PDRETAASLL
0451 QAGYKGRVTG WGNLKETWTA NVGKGQPSVL QVVNLPIVER
     PVCKDSTRIR
0501 ITDNMFCAGY KPDEGKRGDA CEGDSGGPFV MKSPFNNRWY
     QMGIVSWGEG
0551 CDRDGKYGFY THVFRLKKWI QKVIDQFGE
```

[Prothrombin-derived peptide THRB]
(SEQ ID NO: 2)
TATSEYQTFF NPR

As described above, it was shown that the THRB of SEQ ID NO: 2 is useful as a biomarker for detecting cognitive dysfunction diseases. By directly measuring the presence level thereof in serum by mass spectrometry or other methods, such as immunological or enzymological methods, using a liquid chromatography and/or other appropriate separation means or without using the same, the cognitive dysfunction diseases, such as AD and MCI, can be discriminated on diagnosis.

<Production of THRB Marker Peptide Specific Monoclonal Antibody>

An antigen peptide was synthesized in order to create a specific antibody recognizing the Prothrombin precursor-derived peptide THRB of SEQ ID NO: 2. For the synthetic peptide, a cysteine residue was added to the C-terminal in order to be bound to a carrier protein.

A peptide (TATSEYQTC-KLH, see the description later) bound to the carrier protein was mixed with an adjuvant, and then immunized to a mouse. About two weeks later, additional immunization was performed. Three weeks later, lymphocytes were isolated from the iliac lymph node, cell fusion with myeloma was performed, and then hybridoma culture was started.

A culture supernatant was measured by an enzyme immunoassay method (EIA method), a hybridoma showing positivity was selected, and single cloning was performed. A large amount of the single cloned hybridoma was cultured, and then a specific antibody was purified using a Protein G column.

The sequence of the synthetic antigen peptide for creating the specific antibody is shown below. The cysteine residue (C) on the C-terminal of an underline portion was added in order to be bound to the carrier protein.

[Synthetic antigen peptide]
(SEQ ID NO: 3)
TATSEYQTC

INDUSTRIAL APPLICABILITY

Since cognitive dysfunction diseases including mild cognitive impairment and Alzheimer's disease can be detected using the biomarker disclosed in the present invention, the present invention is applicable to the use in the diagnostic field including a diagnostic agent.

The invention claimed is:

1. A method for diagnosing a cognitive dysfunction disease in a subject comprising:
   preparing a biological sample extracted from the subject;
   processing the biological sample with acid treatment;
   processing the acid-treated biological sample by ultrafiltration;
   detecting a peptide consisting of an amino acid sequence represented by SEQ ID NO: 2, wherein the detecting is performed by a mass spectrometry method or an immuno-MS method, in the biological sample, and
   diagnosing the subject with the cognitive dysfunction disease when a positive detecting is obtained,
   wherein the mass spectrometry method is a 2D-LC-MALDI TOF-MS method or LC-MS/MS method and the cognitive dysfunction disease is mild cognitive impairment or Alzheimer's disease.

2. A method for diagnosing a cognitive dysfunction disease in a subject comprising:
   providing a separate subject having the cognitive dysfunction disease;
   preparing a first biological sample extracted from the separate subject having the cognitive dysfunction disease;
   preparing a second biological sample extracted from the subject to be diagnosed;
   processing the first biological sample and second biological sample respectively with acid treatment;
   processing the acid-treated first biological sample and second biological sample respectively by ultrafiltration;
   measuring the amount of a peptide consisting of an amino acid sequence represented by SEQ ID NO: 2, wherein the measuring is performed by a mass spectrometry method or an immuno-MS method, both in the first biological sample and in the second biological sample; and
   diagnosing the subject with the cognitive dysfunction disease when, by comparing the measured amount from the first biological sample with that from the second biological sample, there is no statistical difference between the two,
   wherein the mass spectrometry method is a 2D-LC-MALDI TOF-MS method or LC-MS/MS method and the cognitive dysfunction disease is mild cognitive impairment or Alzheimer's disease.

* * * * *